(12) United States Patent
Chung et al.

(10) Patent No.: US 10,285,640 B2
(45) Date of Patent: May 14, 2019

(54) PROCESS AND METHOD FOR FABRICATING WEARABLE AND FLEXIBLE MICROFLUIDIC DEVICES AND SYSTEMS

(71) Applicant: SIMON FRASER UNIVERSITY, Burnaby (CA)

(72) Inventors: Daehan Chung, Coquitlam (CA); Bonnie Gray, Vancouver (CA)

(73) Assignee: Simon Fraser University, Burnaby, British Columbia (CA)

( * ) Notice: Subject to any disclaimer, the term of this patent is extended or adjusted under 35 U.S.C. 154(b) by 0 days.

(21) Appl. No.: 15/331,665

(22) Filed: Oct. 21, 2016

(65) Prior Publication Data

US 2017/0128008 A1 May 11, 2017

Related U.S. Application Data

(60) Provisional application No. 62/244,716, filed on Oct. 21, 2015.

(51) Int. Cl.
| | |
|---|---|
| *B32B 3/10* | (2006.01) |
| *A61B 5/00* | (2006.01) |
| *B32B 3/26* | (2006.01) |
| *B32B 3/30* | (2006.01) |
| *B32B 5/02* | (2006.01) |
| *B32B 27/12* | (2006.01) |
| *B32B 27/30* | (2006.01) |
| *A61B 5/15* | (2006.01) |

(52) U.S. Cl.
CPC .............. *A61B 5/6804* (2013.01); *A61B 5/15* (2013.01); *B32B 3/266* (2013.01); *B32B 3/30* (2013.01); *B32B 5/02* (2013.01); *B32B 27/12* (2013.01); *B32B 27/304* (2013.01); *A61B 2562/028* (2013.01); *A61B 2562/12* (2013.01)

(58) Field of Classification Search
CPC ....... A61B 5/15; A61B 2562/08; B32B 3/266; B32B 3/30; B32B 27/12; B32B 27/304
USPC .......................................... 428/166–169, 188
See application file for complete search history.

(56) References Cited

U.S. PATENT DOCUMENTS

| | | | |
|---|---|---|---|
| 5,262,444 A * | 11/1993 | Rusincovitch | .......... B32B 27/22 521/50.5 |
| 2013/0095506 A1* | 4/2013 | Bhandari | .......... B01L 3/502707 435/7.92 |
| 2015/0132742 A1* | 5/2015 | Thuo | .................. B01L 3/502707 435/5 |

(Continued)

OTHER PUBLICATIONS

Kutz, Applied Plastics Engineering Handbook: Processing and Materials, 2011, Andrew William, pp. 71-72 (Year: 2011).*

(Continued)

*Primary Examiner* — Maria V Ewald
*Assistant Examiner* — Zachary M Davis
(74) *Attorney, Agent, or Firm* — Palmer IP Inc.

(57) ABSTRACT

A new fabrication process for flexible and wearable microfluidic channel structures and devices is provided. Microfluidic channel structures and devices can be printed on textiles and in particular on flexible fabrics, such as clothing, for applications in wearable microfluidic sensors and systems. The wearable and flexible microfluidic devices are fabricated from water-insoluble plastisol polymers, which may be screen-printable, and sheets of paper may be used as a sacrificial substrate during production.

4 Claims, 12 Drawing Sheets

(56) References Cited

U.S. PATENT DOCUMENTS

| | | | | |
|---|---|---|---|---|
| 2016/0089671 | A1* | 3/2016 | Karam | B01L 3/502707 422/502 |
| 2016/0116427 | A1* | 4/2016 | Laurenson | G01N 27/327 422/82.01 |
| 2017/0173578 | A1* | 6/2017 | Crooks | G01N 21/78 |

OTHER PUBLICATIONS

Guan et al., "Chemiluminescense detection for microfluidic cloth-based analytical devices", Apr. 21, 2015, Biosensors and Bioelectronics, pp. 114-120 (Year: 2015).*

Nie et al., "An integrated flex-microfluidic-Si chip device towards sweat sensing applications," Sensors and Actuators B 227 (2016) 427-437.

Rahimi, et al., "Directly embroidered microtubes for fluid transport in wearable applications," Lab Chip 2017, 17, 1585.

Nie et al. "Electrochemical sensing in paper-based microfluidic devices," Lab Chip, 2010, 10, 477-483.

Guan et al., "Electrochemiluminescence detection in microfluidic cloth-based analytical devices," Biosensors and Bioelectronics 75 (2016) 247-253.

Yeo et al., "Emergence of microfluidic wearable technologies," Lab Chip, 2016, 16, 4082.

Nilghaz et al., "Flexible microfluidic cloth-based analytical devices using a low-cost wax patterning technique," Lab Chip, 2012, 12, 209.

Benito-Lopez et al., "Pump Less Wearable Microfluidic Device for Real Time pH Sweat Monitoring," Procedia Chemistry 1 (2009) 1103-1106.

Dong et al., "Screen-printed microfluidic device for electrochemical immunoassay," Lab Chip, 2007, 7, 1752-1758.

Zhu et al., "Screen-printed microfluidic dielectrophoresis chip for cell separation," Biosensors and Bioelectronics 63 (2015) 371-378.

Choi et al., "Thin, Soft, Skin-Mounted Microfluidic Networks with Capillary Bursting Valves for Chrono-Sampling of Sweat," Adv. Healthcare Mater. 2017, 6, 1601355.

Liu et al., "Understanding wax screen-printing: A novel patterning process for microfluidic cloth-based analytical devices," Analytica Chimica Acta 891 (2015) 234-246.

Feng et al., "Universal Concept for Fabricating Micron to Millimeter Sized 3-D Parylene Structures on Rigid and Flexible Substrates," Micro Electra Mechanical Systems, 2003. MEMS-03 Kyoto. IEEE The Sixteenth Annual International Conference.

Stoppa et al., "Wearable Electronics and Smart Textiles: A Critical Review," Sensors 2014, 14, 11957-11992.

Yeo et al., "Wearable tactile sensor based on flexible microfluidics," Lab Chip, 2016, 16, 3244.

* cited by examiner

FIG. 1

X-SECTIONAL VIEW　　　　PLAN VIEW

X-SECTIONAL VIEW        PLAN VIEW

X-SECTIONAL VIEW  PLAN VIEW

X-SECTIONAL VIEW        PLAN VIEW

X_SECTIONAL VIEW  PLAN VIEW

X-SECTIONAL VIEW          PLAN VIEW

X-SECTIONAL VIEW    PLAN VIEW

PROCESS AND METHOD FOR FABRICATING WEARABLE AND FLEXIBLE MICROFLUIDIC DEVICES AND SYSTEMS

CROSS REFERENCE TO RELATED APPLICATIONS

This application is related and claims priority to U.S. Provisional Patent Application Ser. No. 62/244,716 filed Oct. 21, 2015 and entitled "Process And Method For Fabricating Wearable And Flexible Microfluidic Devices and Systems", which is hereby incorporated herein by reference in its entirety for all purposes.

TECHNICAL FIELD

The present disclosure relates generally to the field of microfluidic devices and sensors. More particularly, the present disclosure relates to fabrication processes for making wearable and/or flexible microfluidic devices and systems.

BACKGROUND

Microfluidics, the technology of manipulating small fluid volumes, has been widely used for many applications in biomedicine, labs-on-a-chip (LOC) analysis, and cell biology, among others. Traditionally, microfluidic devices have been fabricated in solid materials such as silicon or glass using photolithography techniques. In some such conventional embodiments, the solid substrate materials may typically be substantially inflexible and/or exhibit very limited flexibility. While photolithography has enabled the development of microfluidic channels and devices in micro-scale, the use of photolithographic techniques to fabricate microfluidic devices has typically required at least one of expensive equipment, long fabrication time, and complex processes.

As flexible technologies have been introduced and developed for microfabrication, polymers such as polydimethylsiloxane (PDMS) have been commonly used, and PDMS in particular has been popular for such use due to its low toxicity, thermal stability, and low cost. Also, development of soft lithography techniques such as microcontact printing, replica molding, or microtransfer molding, which typically utilize polymers, has enabled fabrication of more flexible microfluidic channels and devices in micro-scale. However, such polymer based microfluidic channels and devices have been typically bonded to silicon or glass substrates in systems using such soft lithographic techniques. Although PDMS itself is mechanically flexible, the use of rigid substrates has hindered development of fully flexible microfluidic devices that can conform to curved surfaces.

In addition to flexible technology, more specifically wearable technology has become of significant interest in recent years. The use of microfluidic sensors and monitoring systems on clothes or other wearable items are desired for their potential to improve human life. For example, wearable motion sensors may be desirable for use in rehabilitation, and wearable biosensors may be desirable for use in real-time bio-signal monitoring. However, a desire remains for improved production techniques for enabling fabrication of fully wearable and flexible microfluidic devices or systems on textiles or other flexible substrates. Some development of certain flexible microfluidic devices such as pH sensors or biosensors have been proposed using paper-based flexible microfluidic devices technologies. In some such cases, paper is for forming fluidic microchannels, however, typical such paper-based fluidic channels are not sufficiently durable and typically cannot be used repeatedly, making them unsuitable for many wearable applications or for integration with clothing.

In view of the foregoing, there remains a need for new and improved fabrication processes and devices that enable production and implementation of flexible and wearable microfluidic devices and sensors, and in particular, flexible and wearable microfluidic devices and sensors which may be implemented on textile or other flexible substrates without hindering the flexibility of the textile. There additionally remains a need for improved microfluidic fabrication processes which address some of the limitations of existing techniques and devices, such as improved processes and devices which may desirably provide one or more of improved efficiency, increased speed, reduced cost and increased simplicity of microfluidic device production.

SUMMARY

It is an object of the present invention to provide microfluidic devices and corresponding fabrication processes that address some of the limitations of the prior art. According to one embodiment of the present invention, new fabrication processes for producing wearable microfluidic channels and devices are provided. In one such embodiment, a new printing-based fabrication process for producing microfluidic channels and devices on fabric or other similar textiles is provided. In one embodiment, plastisol materials, including plastisol inks, may be applied by coating or printing to fabricate flexible and/or wearable microfluidic channel structures and devices applied to textile or other flexible substrate materials. Plastisols are defined as polymer-based substances which comprise resin and plasticizer components in a liquid or gel-like phase and can be converted to a solid phase by application of heat. For the purposes of this disclosure, the term plastisol encompasses the general category of thermally curable liquid/gel to solid materials suitable for application to flexible substrates such as by printing, including but not limited to plastisols comprising thermoplastic polymers and polyvinylchloride (PVC) based polymers, for example.

In a first embodiment, a method for fabricating a microfluidic channel structure is provided comprising: coating a plastisol ink on a first sacrificial substrate to form a first plastisol layer; patterning a microfluidic channel in said first plastisol layer to form a first microfluidic channel layer; coating a plastisol ink on a second sacrificial substrate to form a second plastisol layer; patterning at least one microfluidic opening in said second plastisol layer to form a top plastisol layer; coating a plastisol ink on a textile substrate to form a plastisol bottom layer; bonding said first microfluidic channel layer to said plastisol bottom layer and removing said first sacrificial substrate; and bonding said top plastisol layer to said microfluidic channel layer and removing said second sacrificial substrate to form said microfluidic channel structure.

In one such embodiment, the plastisol ink may comprise a thermoplastic polymer, and in an aspect, at least one of the first and second sacrificial substrates may comprise paper. In another aspect, the plastisol ink may be coated using a screen printing coating process. In a further aspect, patterning at least one of the first and second plastisol layers may comprise laser cutting of the plastisol layer, and in a particular embodiment, the laser cutting may be conducted through the sacrificial substrate, such as to control a dimension (such as width or depth) of the pattern cut into the plastisol layer. In one aspect, coating the plastisol ink to form first and second plastisol layers may further comprise heating the plastisol ink to thermally cure the first and second plastisol layers. In another aspect, at least one of the bonding of the first microfluidic channel layer to the bottom plastisol layer and the bonding of the top plastisol layer to the first microfluidic channel layer may comprise thermally fusion bonding under application of pressure.

In one aspect, the textile substrate to which the plastisol ink is coated may comprise at least one of: a flexible fabric, a flexible mesh, and a flexible film substrate. In a further aspect, coating of the plastisol ink to form the first and second plastisol layers may further comprise planarization of at least one of the first and second plastisol layers, such as by application of pressure under a substantially planar surface at a temperature above a plastic deformation threshold temperature of the plastisol material, followed by cooling of the plastisol layer to a temperature under the plastic deformation threshold temperature of the plastisol.

In one embodiment, the patterning of the at least one microfluidic opening in the second plastisol layer to form a top plastisol layer may further comprise patterning at least one of a microfluidic inlet and a microfluidic outlet in the second plastisol layer to form the top plastisol layer. In another embodiment, bonding of the first microfluidic channel layer to the bottom plastisol layer may comprise thermally fusing the first microfluidic channel layer to the bottom plastisol layer using at least one of a heated lamination plate and a heated roller laminator. In one aspect, bonding of the top plastisol layer to the first microfluidic channel layer may comprise thermally fusing the top plastisol layer to the first microfluidic channel layer using at least one of a heated lamination plate and a heated roller laminator.

In another embodiment, patterning a microfluidic channel in the first plastisol layer to form a first microfluidic channel layer may further comprise patterning a plurality of microfluidic channels in the first plastisol layer to form a first microfluidic channel layer comprising a plurality of microfluidic channels. In a further embodiment, patterning a microfluidic channel in the first plastisol layer to form a first microfluidic channel layer may further comprise patterning a plurality of microfluidic channels in the first plastisol layer to form a plurality of microfluidic channel layers, where each microfluidic channel layer comprises at least one microfluidic channel, and where bonding the first microfluidic channel layer further comprises sequentially bonding the plurality of microfluidic channel layers to the plastisol bottom layer and sequentially removing the first sacrificial substrate from each of the plurality of microfluidic channel layers.

In another embodiment, a flexible microfluidic channel structure is provided, which comprises: a bottom plastisol layer coated on a textile substrate; at least one microfluidic channel layer comprising a plastisol layer patterned with at least one microfluidic channel, and bonded to the bottom plastisol layer; a top plastisol layer comprising at least one microfluidic opening, and bonded to the at least one microfluidic channel layer; wherein the at least one microfluidic opening is fluidly connected to the at least one microfluidic channel. In one such embodiment, the textile substrate may comprise at least one of: a flexible fabric, a flexible mesh, and a flexible film substrate. In another such embodiment, the plastisol may comprise a thermoplastic polymer. In a further embodiment, at least one of the microfluidic channel layer(s) and the top plastisol layer are thermal fusion bonded, or thermally fused, to at least one of the bottom plastisol layer and the at least one microfluidic channel layer. In another embodiment, the microfluidic opening may comprise at least one of a microfluidic inlet and a microfluidic outlet, and is fluidly connected to at least one of the microfluidic channels.

In one embodiment, a plastisol, such as a screen printable plastisol ink may be used for fabricating the flexible microfluidic channel structures and devices. In one aspect, a screen printable plastisol ink may be chosen for the fabrication of our wearable microfluidic devices because certain suitable plastisol inks have properties that make them well-suited for flexible, and/or wearable applications. In one such application, a plastisol ink comprising a thermoplastic polymer which is highly flexible may desirably be chosen. In another aspect, a suitable plastisol ink may desirably also be washable an exhibit non water-soluble and hydrophobic properties as may be suitable for use in wearable applications such as applied to clothing. In one embodiment, plastisol ink may be commonly used for screen printing on textiles, and may therefore be desirably designed to provide strong adhesion to fabric. In another aspect, a suitable plastisol ink may desirably not require an additional curing agent (unlike some other flexible materials such as PDMS for example), and thus may desirably be cured quickly, and may desirably simplify coating application to a textile or fabric by a printing process. In one embodiment, these properties may therefore make plastisol inks suitable for the fabrication of flexible and/or wearable microfluidic structures and devices.

In one embodiment, sheets of normal office paper may be used as a sacrificial substrate. The plastisol ink may be coated, such as by printing, on the paper and cured to form a thin plastisol layer, desirably of a substantially uniform thickness. The paper may desirably be dense enough to not absorb the plastisol, and may desirably also be suitable to withstand plastisol curing temperatures.

In one embodiment, the plastisol ink coated papers may be patterned using a pattern cutting machine, such as a laser cutter machine. In one such embodiment, micro-scale structures may be obtained by controlling the power and speed of the cutting laser. In a particular such embodiment, a laser cutter machine may be computer controlled, so as to provide for patterning of precisely dimensioned microfluidic channels and other features. In one aspect, microfluidic channels, inlets, outlets, reservoirs, and/or other microfluidic features may be patterned on the plastisol films to form one or more microfluidic channel layers. In one embodiment, layers of plastisol such as top, channel and bottom layers, may be bonded together using a thermal fusion bonding technique, such as by application of heat under pressure to thermally fuse adjacent plastisol layers to form a microfluidic channel structure and/or device. In one such embodiment, for each layer to layer bonding process, the sacrificial substrate (such as paper) is removed before the bonding step, such as by manual or automated removal means.

BRIEF DESCRIPTION OF THE DRAWINGS

Methods and systems according to embodiments of the present invention will now be described with reference to the accompanying drawing figures, in which.

Like reference numerals refer to corresponding parts throughout the several views of the drawings.

DETAILED DESCRIPTION OF SEVERAL EMBODIMENTS

Figure 1:
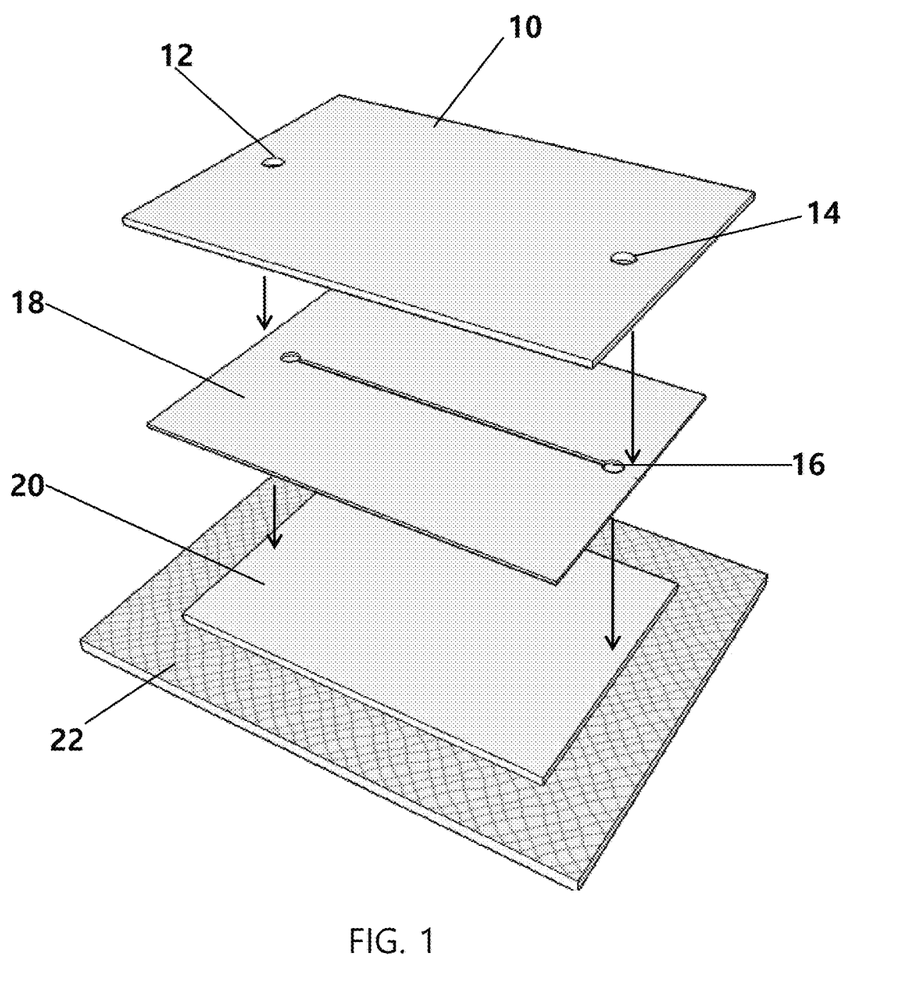
FIG. 1 illustrates a perspective view of a fabrication process for fabrication of an exemplary microfluidic channel design in a wearable microfluidic device, according to an embodiment of the invention.

FIG. 1 illustrates a perspective view of a fabrication process for fabrication of an exemplary basic microfluidic channel 16 design in a wearable microfluidic device, fabricated using plastisol polymer ink materials, according to an embodiment of the present invention. In one such embodiment, each plastisol layer 10, 18, 20, of the microfluidic device may be fabricated and bonded together. In one aspect, an exemplary wearable plastisol ink microfluidic device having a simple one layer microfluidic channel is shown in FIG. 1. In the exemplary one channel structure shown in FIG. 1, a top layer 10 has a fluid inlet 12 and fluid outlet 14, and may be formed of a plastisol polymer ink, such as by the exemplary methods described below and shown in FIGS. 2 to 8. A microfluidic channel 16 is patterned on the exemplary single plastisol polymer channel layer 18, and a plastisol polymer bottom layer 20 is printed on a desired substrate, such as a flexible textile or fabric substrate 22. Three plastisol polymer layers (bottom layer 20, channel layer 16, and top layer 10) are then bonded together to form a wearable and flexible single-layer microfluidic channel structure.

The following description of exemplary embodiments illustrated in FIGS. 2 to 8 are provided showing fabrication of an exemplary simplified single-layer microfluidic channel and associated microfluidic device, and each figure presents both cross-sectional and plan views together of the exemplary device design. In other embodiments, depending on the intended purpose of the microfluidic device, multiple layers including one or more microfluidic channel layers may be provided with different shapes, sizes, orientations and patterns of microfluidic channels, passages, reservoirs, and other microfluidic structures in order to fabricate any suitable desired multi-layer microfluidic device arrangement as may be desired for a wide range uses to which microfluidic devices may be applied.

Figure 2A:
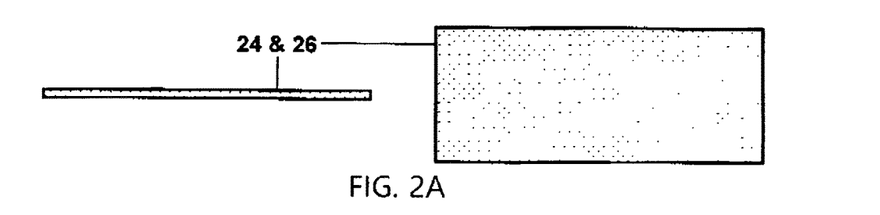
FIGS. 2A, 2B, 2C and 2D each illustrate cross-sectional and plan views of fabrication steps of a process for screen printing a plastisol ink on a sheet of paper, according to an embodiment of the invention.
Figure 2B:
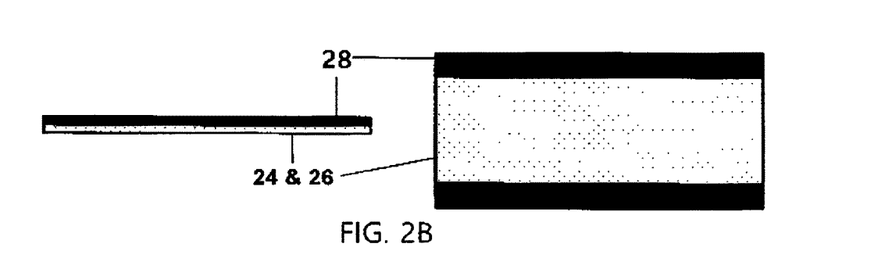
Figure 2C:
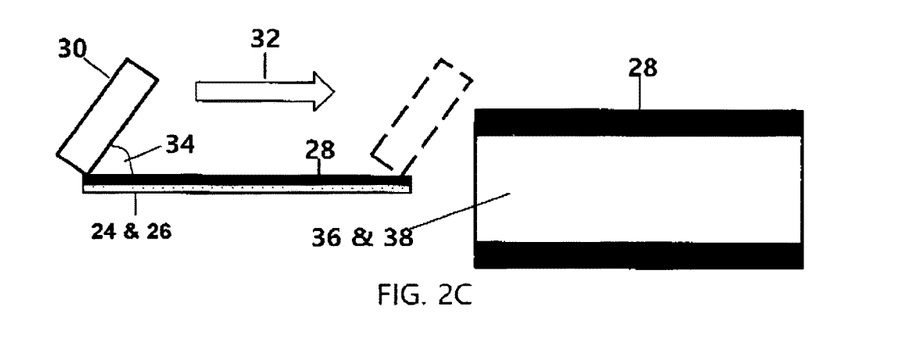
Figure 2D:
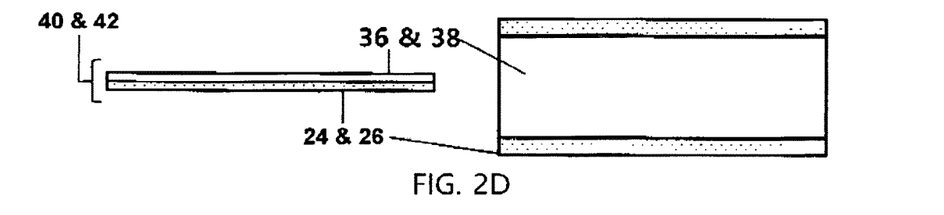

FIGS. 2A, 2B, 2C and 2D each illustrate cross-sectional and plan views of fabrication steps of an exemplary screen printing process 32 for screen printing a plastisol polymer ink on a sheet of paper as an exemplary sacrificial substrate, according to an embodiment of the invention. In other embodiments, other suitable coating methods adaptable for coating a plastisol polymer ink on a desired sacrificial substrate may be used. In the presently described exemplary embodiment, the plastisol ink is coated on sheets of plain paper as a sacrificial substrate using a screen printing method. In one embodiment, such as to fabricate an exemplary single layer microfluidic channel structure, two sheets of normal office paper 24 and 26 are used as an exemplary sacrificial substrate (FIG. 2A). A suitable screen printing screen 28 was placed on the paper 24 and 26 to obtain a desirably substantially uniform thickness of plastisol films 36 and 38. In one embodiment, screen printing process 32 may desirably be used to avoid potential drawbacks of manual printing techniques performed without a screen which may results in undesirably uneven thickness of the plastisol polymer film. In one aspect, any suitable kind of physical screen with open areas on it can be used as screen printing screen 28. Once the screen 28 is placed on paper 24 and 26 (FIG. 2B), the plastisol ink 34 may be applied on the paper and in one aspect may then be scraped such as by using a screen printing squeegee 30. In one embodiment, the screen printing technique 32 may desirably enable substantially uniform coating of the plastisol film 36/38 over the sacrificial substrate (paper for example) sheets 24/26 (shown in FIG. 2C). In one aspect, the thickness of the plastisol film 36/38 may desirably be substantially the same as the thickness of the screen, allowing for control and selection of desired plastisol film thickness by appropriate selection of the thickness of the screen 28. After the plastisol 34 is printed as a plastisol film 36/38 on the paper 24/26, the screen is removed, and the plastisol may be thermally cured, such as on a hotplate 44 at a suitable curing temperature and duration (such as in one aspect at about 110° C. for 20 seconds) and subsequently cooled down, such as to room temperature, to form a cured plastisol/paper film 40/42 (FIG. 2D).

Figure 3A:
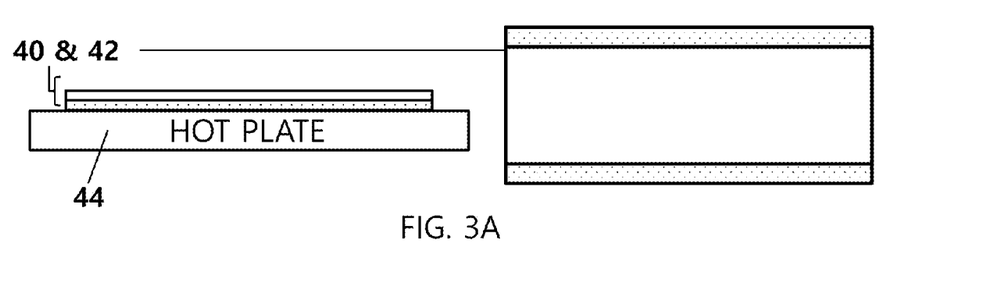
FIGS. 3A and 3B each illustrate cross-sectional and plan views of fabrication steps of a process for planarization of the plastisol ink and paper film structure shown FIGS. 2A to 2D, in accordance with an embodiment of the invention.
Figure 3B:
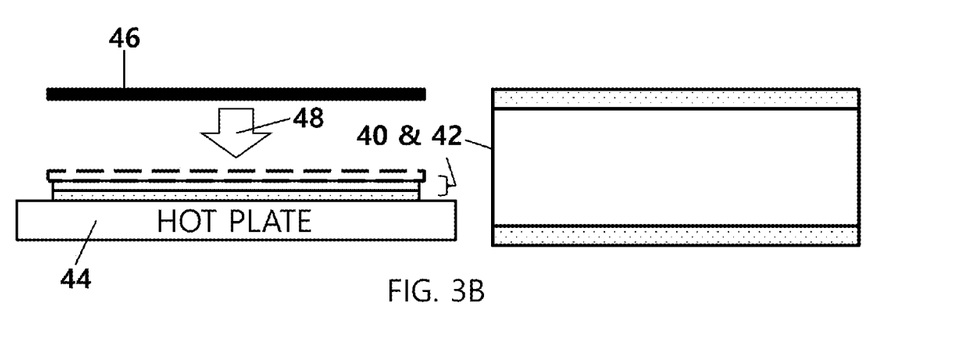

FIGS. 3A and 3B each illustrate cross-sectional and plan views of fabrication steps of a planarization process 48 for planarization of the plastisol ink and paper film structure shown in FIGS. 2A to 2D (numbered as 36 and 38 in FIGS. 2A to 2D), in accordance with an embodiment of the invention. The planarization process 48 may be performed to make the plastisol film 36 and 38 coated in the step described above into a substantially flat or planar plastisol film/substrate 40/42, and to desirably prevent any air gap between plastisol films after the subsequent bonding process(es).

In one embodiment, a planarization process 48 may comprise heating of the coated plastisol/sacrificial substrate (such as paper as a sacrificial substrate in one example) film 40/42 under application of pressure from a substantially planar surface 46 so as to plastically conform the plastisol/sacrificial substrate film 40/42 to the planar surface at a temperature above a plastic transition temperature of the plastisol, followed by cooling the plastisol/sacrificial substrate file 40/42 to a temperature below the plastic transition temperature of the plastisol, so as to maintain the substantially planar form of the plastisol/sacrificial substrate file 40/42 for subsequent bonding steps detailed below. In a particular embodiment, a planarization process 48 may comprise heating an exemplary coated plastisol/paper film 40/42 by placing on a hotplate 44 heated at for example 125° C. (as shown in FIG. 3A), and a substantially planar glass microscope slide 46 is placed on the plastisol/paper film 40/42, and pressure is applied to the glass slide 46 such as by using a weight of approximately 2 kg (such as a 2 kg book in one example) for a period of approximately 20 seconds, after which the plastisol/paper film 40/42 is cooled slowly to room temperature for example (as shown in FIG. 3B). In one such exemplary embodiment, the weight applied to the glass slide 46 may be kept in place to maintain pressure on the plastisol/paper film 40/42 during the cooling process.

Figure 4A:
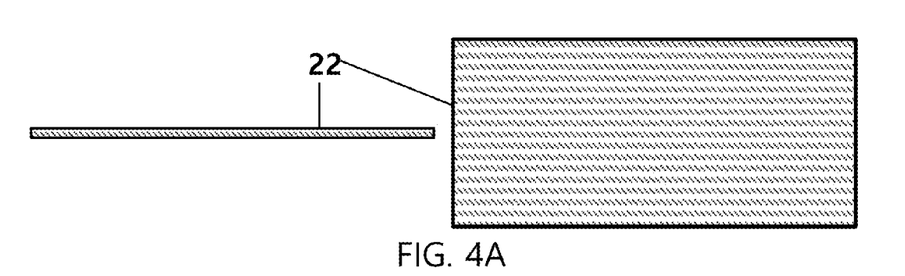
FIGS. 4A, 4B, 4C and 4D each illustrate cross-sectional and plan views of fabrication steps of a process of screen printing a bottom layer of a microfluidic device on a textile, according to an embodiment of the present invention.
Figure 4B:
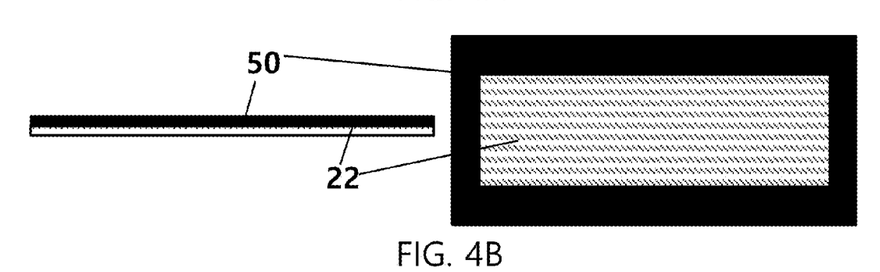
Figure 4C:
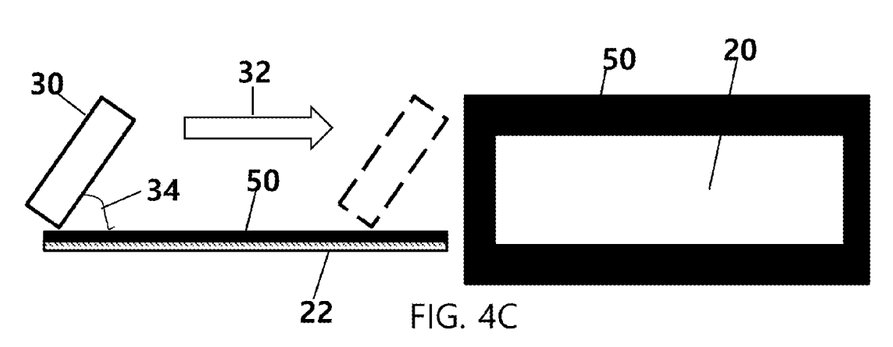
Figure 4D:
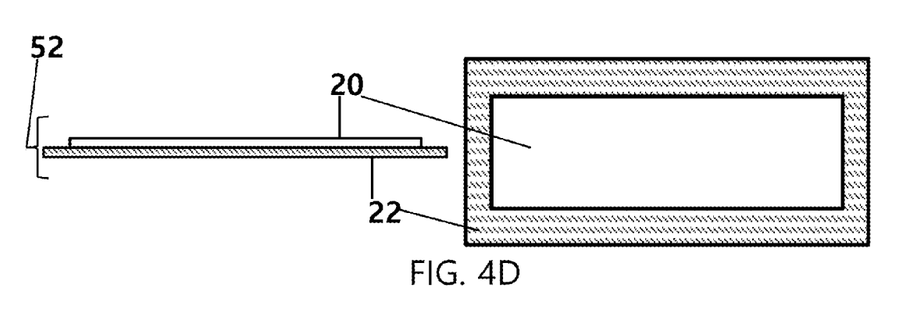

FIGS. 4A, 4B, 4C and 4D each illustrate cross-sectional and plan views of fabrication steps of a coating process such as screen printing process 32, for forming a plastisol bottom layer 20 of a microfluidic structure or device on a textile substrate 22, according to an embodiment of the present invention. In one such embodiment, the textile substrate 22 may comprise a flexible fabric 22 which may be placed on a flat surface suitable for screen printing, and a screen printing screen 50 is placed on the fabric (FIG. 4B). In one embodiment, a substantially similar screen printing technique to that shown as screen printing process 32 in FIGS. 2A to 2D and explained above, is performed, to coat the bottom plastisol layer 20 by printing. The plastisol ink 34 is applied on the fabric substrate 22 and scraped such as by using a screen printing squeegee 30 (FIG. 4C). After screen printing the bottom plastisol layer 20, plastisol/fabric film 52 may be thermally cured, such as on a hotplate 44 at a suitable curing temperature and duration (such as in one aspect at about 110° C. for 20 seconds) and subsequently cooled down, such as to room temperature, to form a cured plastisol/fabric film 52 (FIG. 4D).

Figure 5A:
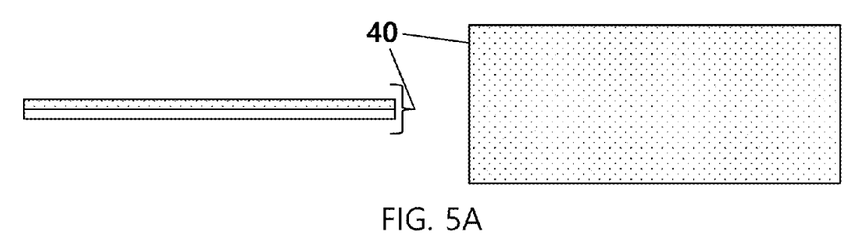
FIGS. 5A, 5B and 5C each illustrate cross-sectional and plan views of fabrication steps of a process of patterning a channel layer of the plastisol ink/paper film structure shown in FIGS. 2A to 2D using a laser cutter, according to an embodiment of the invention.
Figure 5B:
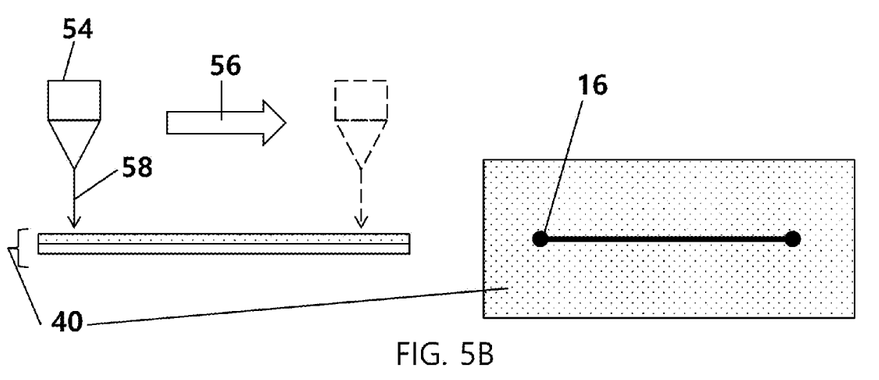
Figure 5C:
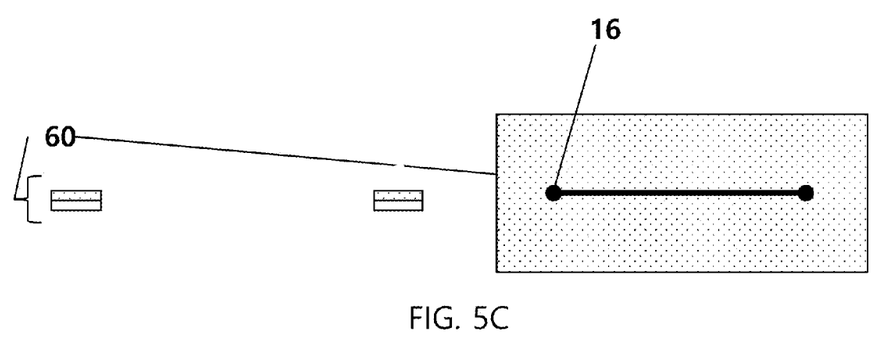

FIGS. 5A, 5B and 5C each illustrate cross-sectional and plan views of fabrication steps of a patterning process 56 for patterning a channel layer 60 of the plastisol ink/paper film structure 40 (shown in FIGS. 2A to 2D as 36/38), according to an embodiment of the invention. In one such embodiment, a laser cutter 54 may be used for patterning one or more microfluidic channel or other microfluidic features in the plastisol/paper film layer 40. In one aspect, the plastisol/paper film 40 may be placed on a suitable laser cutter machine 54 (FIG. 5A), and the laser beam 58 from the laser cartridge of the laser cutter 54 may be used to ablate and/or burn the paper and plastisol film 40 together to pattern a microfluidic channel 16 or other microfluidic feature on the plastisol/paper film 40 (FIG. 5B). In one embodiment, a laser cutting patterning process 56 is very useful technique for patterning, and the power and speed of the laser beam 58 may be desirably controlled to obtain desired dimensions (such as width and depth) of patterning, such as in one aspect to control or minimize the channel dimension. In one embodiment, when laser power is too high and speed is too low, the laser beam 58 may ablate/burn the paper and melts the plastisol more, which may result in a deeper, wider or larger channel dimension than may be desirable. In another aspect, if the laser power is too low and speed is too high, the plastisol film 40 may not be sufficiently cut.

In one embodiment, the microfluidic channel layer 60 may be prepared by patterning the microfluidic channel 16 on the plastisol/paper film 40 with an automated and/or computer controlled laser cutter machine 54.

Figure 6A:
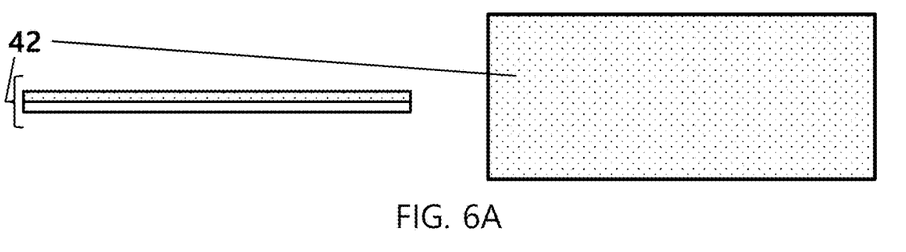
FIGS. 6A, 6B and 6C each illustrate cross-sectional and plan views of fabrication steps of a process of patterning a top layer of the plastisol ink/paper film structure shown in FIGS. 2A to 2D using a laser cutter, according to an embodiment of the invention.
Figure 6B:
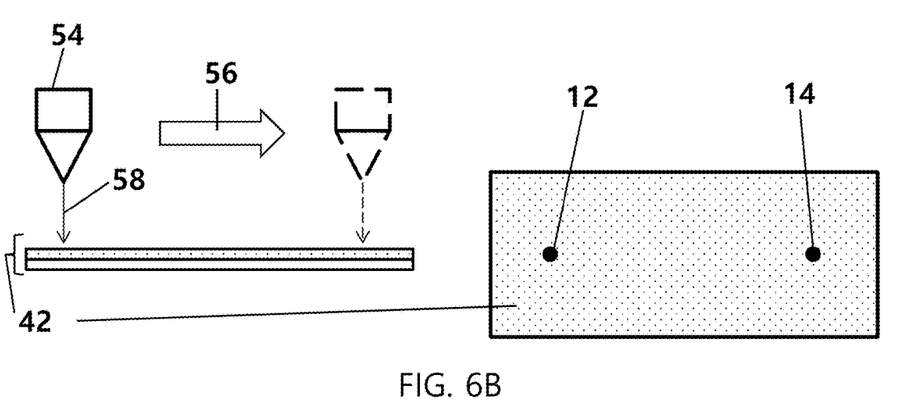
Figure 6C:
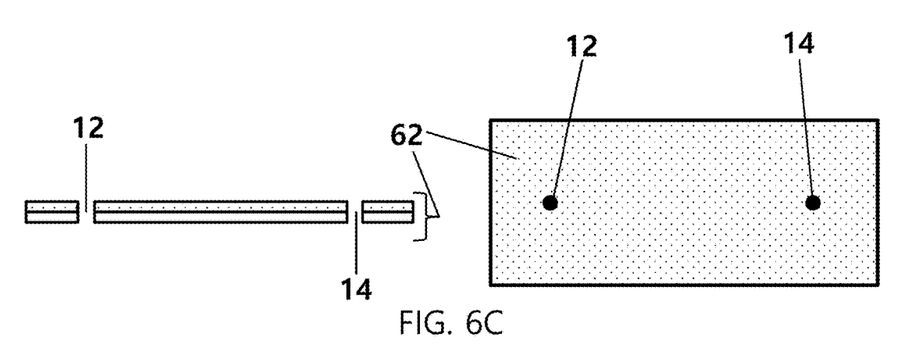

FIGS. 6A, 6B and 6C each illustrate cross-sectional and plan views of fabrication steps of a patterning process 56 for patterning a top layer 62 of the plastisol ink/paper film structure 42 (shown in FIGS. 2A to 2D as 36/38), according to an embodiment of the invention. In one such embodiment, a laser cutter 54 may be used for patterning one or more microfluidic opening in the plastisol/paper film layer 42 to form top plastisol layer 62. In one such embodiment, substantially the same laser cutting technique 56 may be used to pattern one or more microfluidic openings, such as microfluidic inlet 12 and outlet 14 for a microfluidic channel (such as channel 16 shown in the exemplary channel layer 60 shown in FIG. 5D). In one embodiment, plastisol/paper film 42 is placed on a laser cutter machine 54 (FIG. 6A/6B), and the laser beam 58 is controlled to cut the desired microfluidic opening(s) such as inlet 12 and outlet 14 (FIG. 6B). In one aspect, for the laser cutting of the plastisol/paper film 40 (FIG. 5) and 42 (FIG. 6), the paper substrate side may be placed upward towards the laser beam 58, because typically, the etched structures patterned by the laser cutter 54 may have a "V"-shape etching profile. Accordingly, in such as aspect, the laser beam 58 may melts the surface of the plastisol material and transfers heat to adjacent areas. As a result, the top area of a laser cut layer may typically be burned or ablated more than the bottom area (such forming a cut which is wider nearer the top). In one such aspect, by placing the paper side upward, a desirably minimized plastisol channel dimension can be obtained.

In one embodiment, plastisol top layer 62 may be prepared by patterning one or more microfluidic openings, such as inlet 12 and outlet 14, on the plastisol/paper film 42 with an automated and/or computer controlled laser cutter machine 54 (FIG. 6C).

Figure 7A:
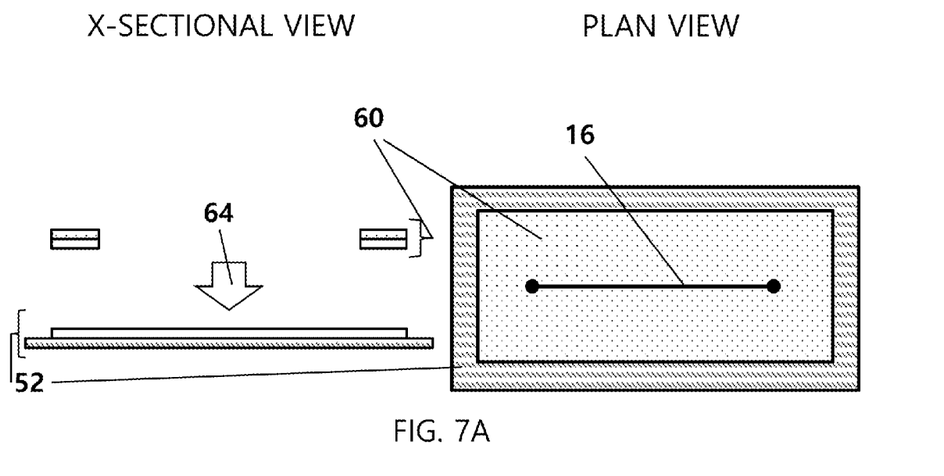
FIGS. 7A and 7B each illustrate cross-sectional and plan views of fabrication steps of a bonding process for bonding a channel layer such as shown in FIGS. 5A to 5C to the bottom layer such as shown in FIGS. 4A to 4D, according to an embodiment of the invention.
Figure 7B:
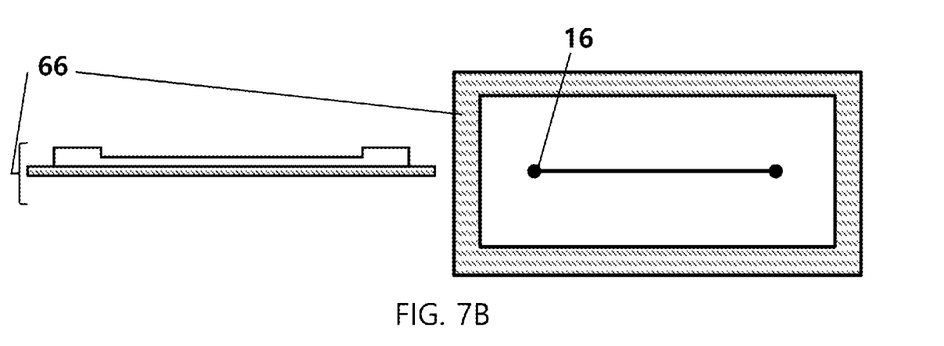

FIGS. 7A and 7B each illustrate cross-sectional and plan views of fabrication steps of a bonding process 64 for bonding a microfluidic channel layer 60 (such as shown in FIGS. 5A to 5C) to a bottom layer 52 (such as shown in FIGS. 4A to 4D), according to an embodiment of the invention. In one aspect, the bonding process is important for successful fabrication of wearable and flexible microfluidic structures and devices. Weak bonding or imperfect bonding may cause malfunction of the devices such as leakage of the liquids. In one embodiment, a thermal fusion bonding process 64 may be used as a preferred method to bond thermoplastic plastisol films such as channel layer film 60 and bottom layer film 52 (FIG. 7A). In one aspect, a thermal laminator may be used to thermally fusion bond plastisol layers to form a microfluidic channel structure. In one such embodiment, to perform thermal fusion bonding, the channel layer 60 and the bottom layer 52 may be heated to make the plastisol film soften. Then the channel layer 60 and the bottom layer 52 may be overlapped, aligned, and pressurized for bonding. This process is repeated until two films are sufficiently and preferably completely bonded or thermally fused together. In one aspect, after thermal fusion bonding by pressurization, the bonded channel and base layer 66 may cooled down, such as to room temperature. In one embodiment, a thermal laminator may be used as in the preferred thermal fusion bonding process 64 because it provides uniform pressure and temperature which enables proper thermal fusion bonding. In another aspect, however, manual bonding methods may also be employed. Thermal fusion bonding is possible because the plastisol is thermoplastic polymer. In one embodiment, after cooling down the bonded structure, the sacrificial substrate (such as paper 24) is detached from the structure (such as by manual or automated means) so that only bonded plastisol base/channel structure 66 remains (FIG. 7B).

Figure 8A:
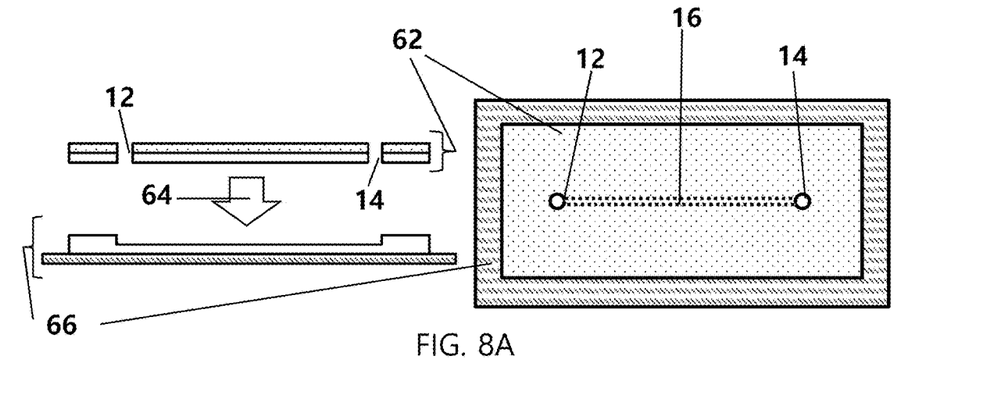
FIGS. 8A and 8B each illustrate cross-sectional and plan views of fabrication steps of a bonding process for bonding a top layer such as shown in FIGS. 6A to 6C to a channel structure such as shown FIGS. 7A and 7B, according to an embodiment of the invention.
Figure 8B:
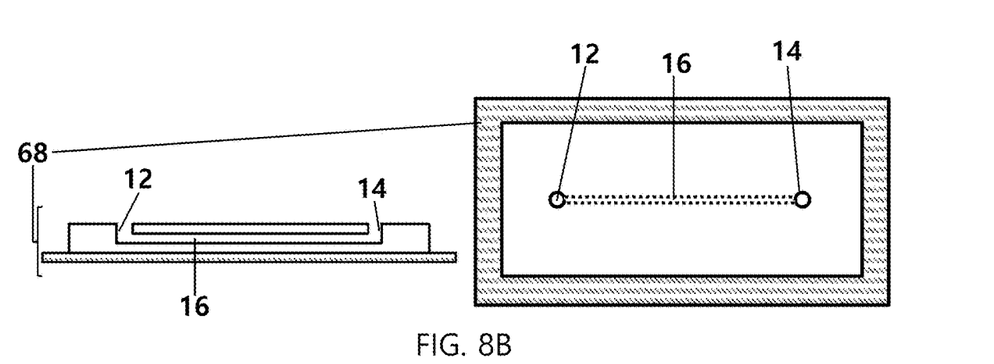

FIGS. 8A and 8B each illustrate cross-sectional and plan views of fabrication steps of a bonding process 64 for bonding a top layer 62 (such as shown in FIGS. 6A to 6C) to a microfluidic channel 66 (such as shown FIGS. 7A and 7B), according to an embodiment of the invention. In one embodiment, substantially the same thermal fusion bonding technique 64 is used to bond the top layer 62 (FIG. 8A). In one aspect, the top layer 62 is bonded to the channel structure 66 to cover and seal the channel 16 and connect it with inlet 12 and outlet 14, and lastly the sacrificial substrate (such as paper 26) is removed so that only the bonded plastisol structure remains on the flexible fabric substrate (FIG. 8B). In one such aspect, a wearable and flexible plastisol microfluidic channel structure 68 may desirably be developed directly on a textile substrate, such as a flexible fabric substrate, according to the fabrication methods according to embodiments of the present invention.

Figure 9:
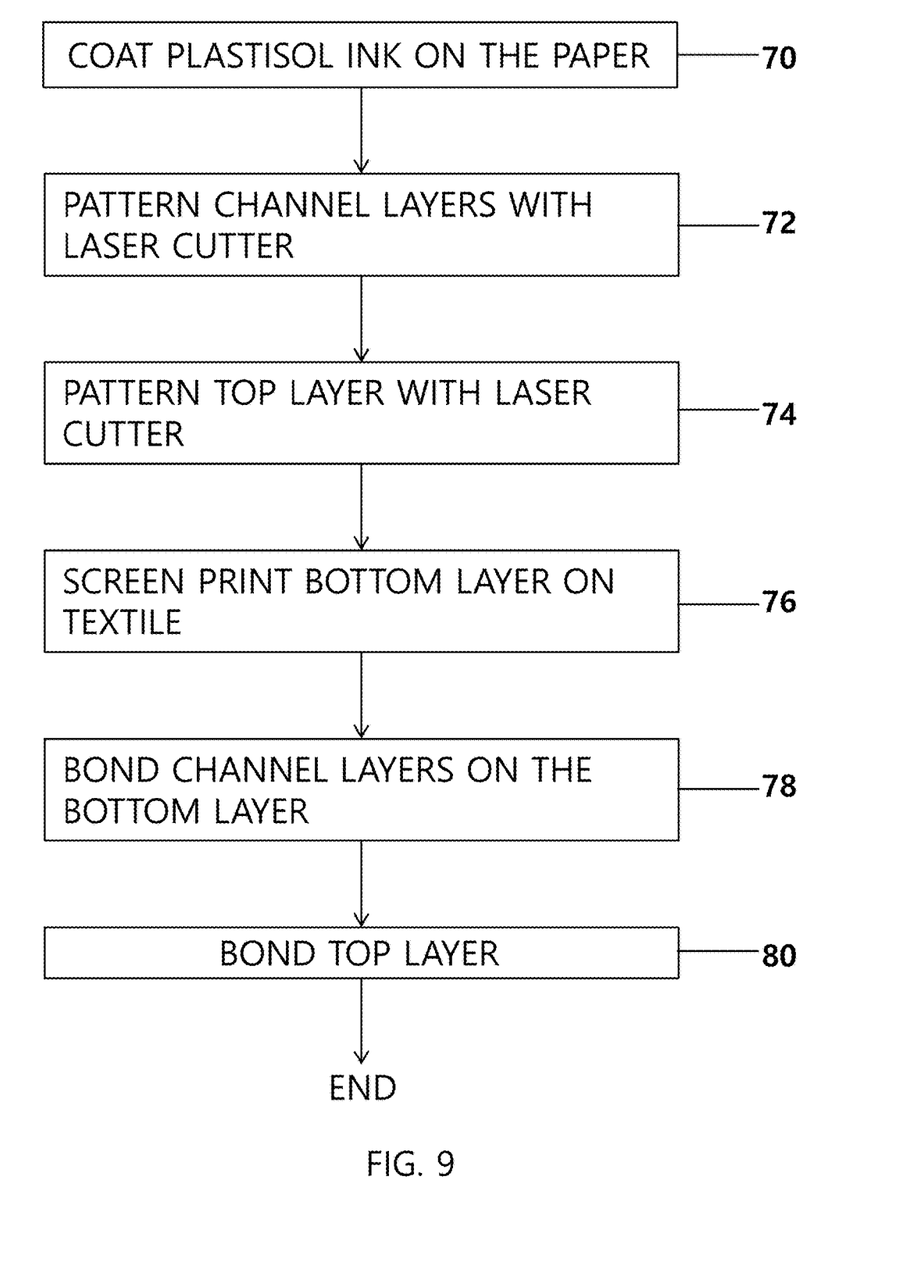
FIG. 9 illustrates a flow diagram illustrating steps of an overall fabrication process for fabricating a flexible microfluidic channel structure, in accordance with an embodiment of the present invention.

FIG. 9 illustrates a flow diagram illustrating steps of an overall fabrication process for fabricating a flexible microfluidic channel structure, in accordance with an embodiment of the present invention. In one embodiment, a first step 70 is to coat a plastisol ink on a sacrificial substrate (such as sheets of paper). Next, pattern the channel layers 72 and top layer 74, such as with a laser cutter machine. In one aspect, multiple channel layers with a variety of microfluidic channel or other feature patterns and shapes can be patterned and used for multi-layer microfluidic devices, depending on the desired purpose. Then the bottom layer is printed on a textile substrate 76, and next, bonding of the channel layers on the bottom layer is performed 78. Lastly, bonding of the top layer on the channel layer(s) is completed 80, to form the microfluidic channel structure in accordance with one embodiment of the invention.

Figure 10A:
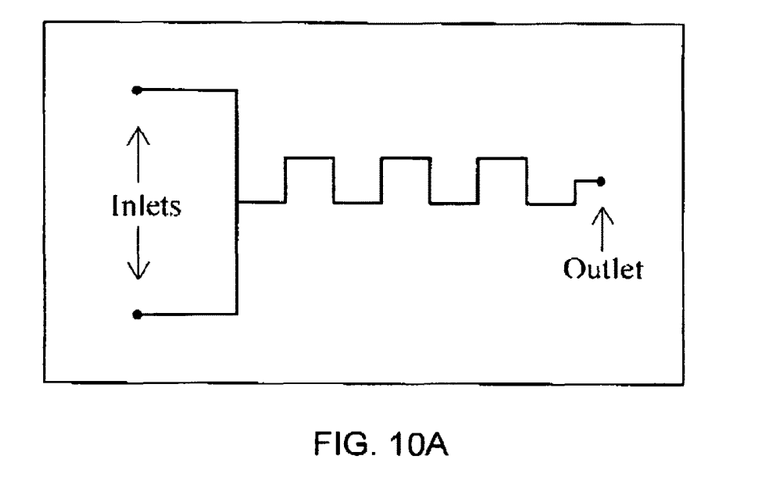
FIG. 10A illustrates a schematic view of an exemplary flexible microfluidic mixer structure design, according to an embodiment of the present invention.

FIG. 10A illustrates a schematic view of an exemplary flexible microfluidic mixer structure design, according to an embodiment of the present invention.

Figure 10B:
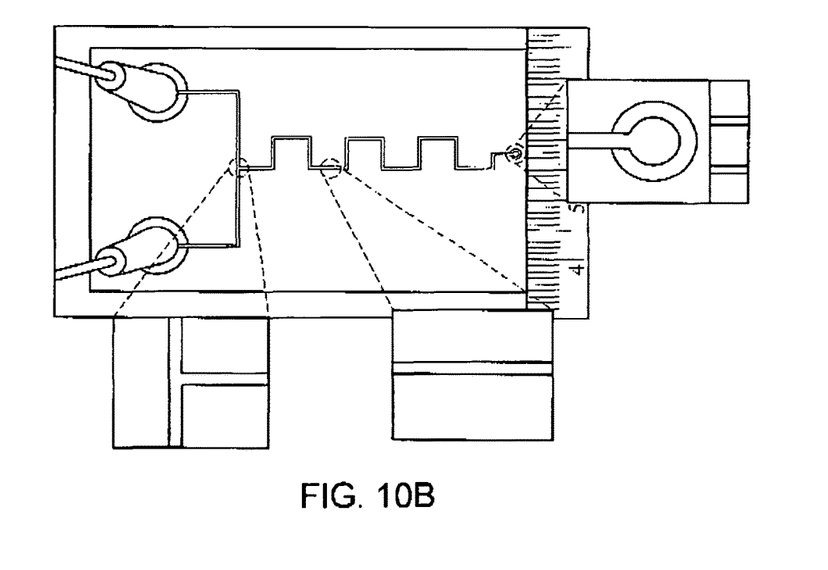
FIG. 10B illustrates a photographic plan view of a fabricated microfluidic mixer structure corresponding to the schematic design shown in FIG. 10A, showing close-up views of portions of the microfluidic channels, according to an embodiment of the present invention.

FIG. 10B illustrates a photographic plan view of a fabricated microfluidic mixer structure corresponding to the schematic design shown in FIG. 10A, showing close-up views of portions of the microfluidic channels, according to an embodiment of the present invention fabricated on a flexible fabric substrate. The exemplary mixer structure as fabricated has dimensions of 70 mm×40 mm×480 µm, has two inlets and one outlet, and is designed that two different types of liquids are combined and flow through one single-layered microfluidic channel. Close-ups of intersection, channel, and outlet are also shown in FIG. 10B. Polyethylene tubes with diameters of 0.86 mm are connected to the inlets using a silicone sealant for liquid injection.

Figure 11:
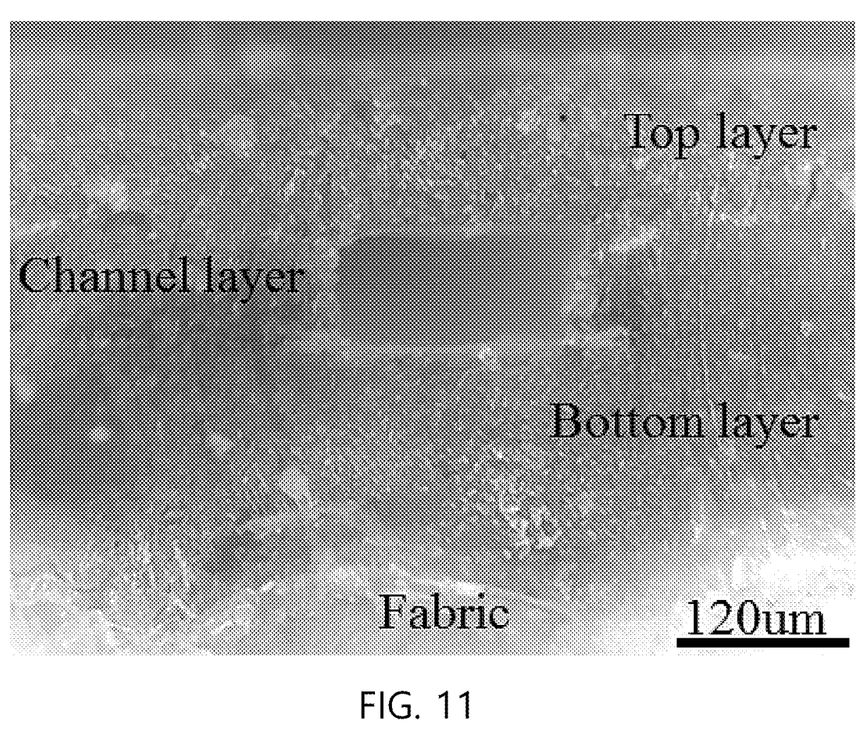
FIG. 11 illustrates a microphotographic cross-sectional view of a fabricated microfluidic channel is a photo of the cross view of the fabricated microfluidic channel, according to an embodiment of the present invention.

FIG. 11 illustrates a microphotographic cross-sectional view of a fabricated microfluidic channel, according to an embodiment of the present invention. Each layer is firmly bonded via thermal fusion bonding, creating a micro-scaled flexible fluidic channel (approximately 120 µm wide and 50 µm deep) on the flexible fabric substrate.

Figure 12A:
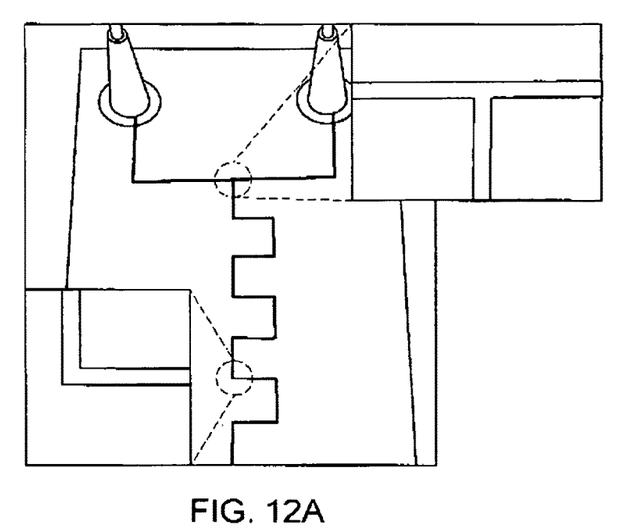
FIG. 12A illustrates a photographic plan view of the fabricated microfluidic mixer structure shown in FIG. 10B in operation on a flat surface, showing close-up views of portions of the microfluidic channels, according to an embodiment of the present invention.

FIG. 12A illustrates a photographic plan view of the fabricated microfluidic mixer structure shown in FIG. 10B in operation on a flat surface, showing close-up views of portions of the microfluidic channels, according to an embodiment of the present invention. In the exemplary shown microfluidic mixer structure, green and red inks are shown being mixed. Close-ups in FIG. 12A show that the green ink and the red ink are clearly separated at the intersection, but the inks are mixed as they flow through the channel.

Figure 12B:
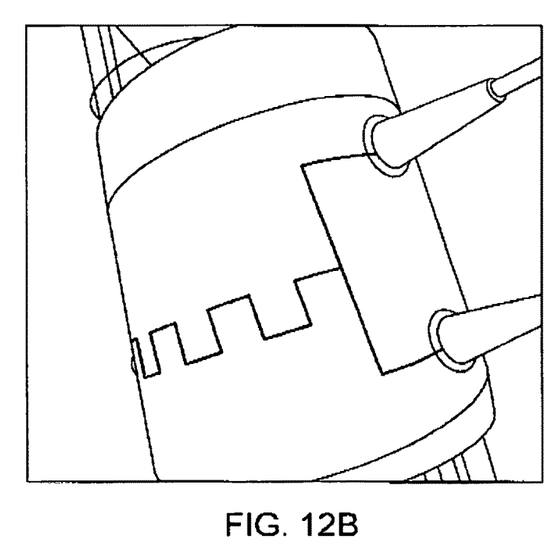
FIG. 12B illustrates a photographic plan view of the fabricated microfluidic mixer structure shown in FIG. 10B in operation, conforming to a curved surface, according to an embodiment of the present invention.

FIG. 12B illustrates a photographic plan view of the fabricated microfluidic mixer structure shown in FIG. 10B in operation, conforming to a curved surface, according to an embodiment of the present invention. In the embodiment shown in FIG. 12B, a cylinder with a diameter of 48 mm is used to attach the mixer to a curved surface. The mixer works properly without any leakage of liquid even on the curved surface. No absorption of liquids into the plastisol polymer is observed due to its hydrophobicity.

Although the preceding description contains details, it should not be considered as limiting the scope of the invention but rather as providing explanation and illustration of the invention. As an example, different shape of channels can be patterned using the laser cutter, and the channel layers can be bonded together to build multi-layered microfluidic devices. As a screen, any kinds of physical masks or screens that have open area on it can be used to print the plastisol. Also, the glass slide used for planarization, or the book used for thermal fusion bonding can be replaced by other flat and heavy materials. Such a variation would not alter the nature of the invention.

While the present invention and its various functional components and operational functions have been described in particular exemplary embodiments, the invention may also be implemented in hardware, software, firmware, middleware or a combination thereof and utilized in systems, subsystems, components or subcomponents thereof, for example, as circuitry that cooperates with the processor to perform various method steps. In particular embodiments implemented at least in part in software, elements of the present invention may be instructions and/or code segments to perform the necessary tasks. The program or code segments may be stored in a machine readable medium, such as a processor readable, such as a processor readable medium or a computer program product, or transmitted by a computer data signal embodied in a carrier wave, or a signal modulated by a carrier, over a transmission medium or communication link. The machine readable medium or processor readable medium may include any medium that can store or transfer information in a form readable and executable by a machine, for example a processor, computer, etc. It will be appreciated that the term "or" as used herein refers to a non-exclusive "or" unless otherwise indicated (e.g., use of "or else" or "or in the alternative").

An embodiment of the present invention relates to a computer storage product with a non-transitory computer-readable medium having computer code thereon for performing various computer-implemented operations. The computer-readable media and computer code may be those specially designed and constructed for the purposes of the present invention, or they may be of the kind well known and available to those having skill in the computer software arts. Examples of computer-readable media include, but are not limited to: programmable logic devices ("PLDs") and ROM and RAM devices including Flash RAM memory storage cards, sticks and chips, for example magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits ("ASICs"), for example. Examples of computer code include machine code, such as produced by a compiler, and files containing higher-level code that are executed by a computer using an interpreter. For example, an embodiment of the invention may be implemented using HTML5, XML, JavaScript, Java, C#, C++, Objective C, or any other suitable known scripting, markup and/or programming languages and development tools. Another embodiment of the invention may be implemented in hardwired circuitry in place of, or in combination with, machine-executable software instructions.

The exemplary embodiments herein described are not intended to be exhaustive or to limit the scope of the invention to the precise forms disclosed. They are chosen and described to explain the principles of the invention and its application and practical use to allow others skilled in the art to comprehend its teachings.

As will be apparent to those skilled in the art in light of the foregoing disclosure, many alterations and modifications are possible in the practice of this invention without departing from scope thereof. Accordingly, the scope of the invention is to be construed in accordance with the substance defined by the claims.

What is claimed is:

1. A flexible microfluidic channel structure comprising:
a bottom plastisol layer coated on a textile substrate;
at least one microfluidic channel layer comprising a plastisol layer patterned with at least one microfluidic channel, and bonded to said bottom plastisol layer for sealing said at least one microfluidic channel along said bottom plastisol layer; and
a top plastisol layer comprising at least one microfluidic inlet and at least one microfluidic outlet, and bonded to said at least one microfluidic channel layer,
wherein said at least one microfluidic inlet and said at least one microfluidic outlet are fluidly connected to said at least one microfluidic channel, permitting a fluid to flow into said at least one microfluidic channel layer from said microfluidic inlet of said top plastisol layer, through said microfluidic channel, and out through said microfluidic outlet of said top plastisol layer.

2. The flexible microfluidic channel structure according to claim 1, wherein said textile substrate comprises at least one of: a flexible fabric, a flexible mesh, and a flexible film substrate.

3. The flexible microfluidic channel structure according to claim 1, wherein said plastisol comprises a thermoplastic polymer.

4. The flexible microfluidic channel structure according to claim 1, wherein at least one of said at least one microfluidic channel layer and said top plastisol layer are thermal fusion bonded to at least one of said bottom plastisol layer and said at least one microfluidic channel layer.

* * * * *